United States Patent [19]

Suzuki

[11] 4,225,486

[45] Sep. 30, 1980

[54] ALOCTIN A

[75] Inventor: Ikuo Suzuki, Owariasahi, Japan

[73] Assignee: Aloace Company Limited, Aichi, Japan

[21] Appl. No.: 961,864

[22] Filed: Nov. 20, 1978

[30] Foreign Application Priority Data

Nov. 21, 1977 [JP] Japan ............................... 52-138907
Feb. 25, 1978 [JP] Japan ................................. 53-20402

[51] Int. Cl.$^2$ ........................ C07G 7/00; A61K 37/00
[52] U.S. Cl. .................................. 260/112 R; 424/177
[58] Field of Search ..................... 260/112 R; 424/177

[56] References Cited

U.S. PATENT DOCUMENTS 3,362,829  1/1968  Landfried, et al. .............. 260/112 R

OTHER PUBLICATIONS

Chem. Abstr., 73, 1970, 75501e.

*Primary Examiner*—Delbert R. Phillips
*Attorney, Agent, or Firm*—Oblon, Fisher, Spivak, McClelland & Maier

[57] ABSTRACT

A glycoprotein isolated from Aloe, a plant belonging to Liliaceae, having a molecular weight of $1.8 \times 10^4$ and a ratio of protein to sugar of 8 to 2 by weight; yielding only a single band upon SDS-polyacrylamide gel electrophoresis without 2-mercaptoethanol treatment and yielding two discrete bands upon SDS-polyacrylamide gel electrophoresis with 2-mercaptoethanol treatment; having hemagglutinating and cytoagglutinating activity for transformed cells; having mitogenic activity for lymphocytes, cap forming activity for lymphocytes and cultured transformed cells using fluorescence labeled glycoprotein; having binding reactivity with some types of serum proteins; and having the capability of activating complement components.

1 Claim, 11 Drawing Figures

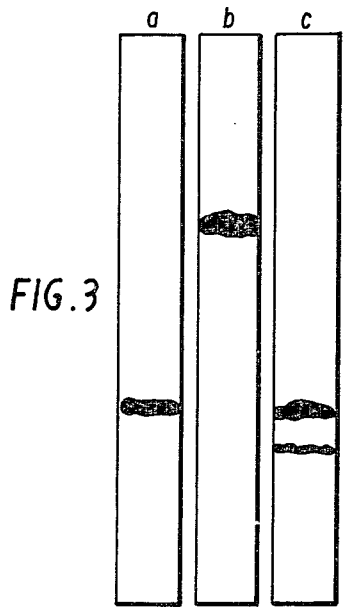

FIG. 3

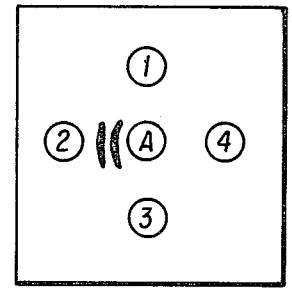

A: NORMAL RABBIT SERUMS
1: β         2: ALOCTIN A
3: S-1       4: S-2

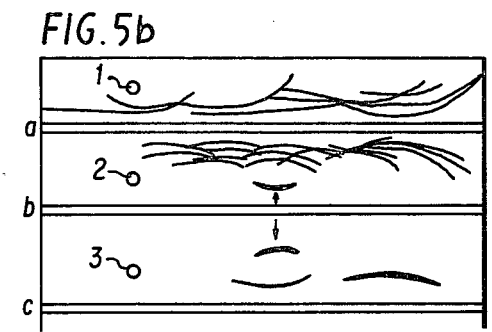

a: RABBIT ANTI-HUMAN SERUM
b: ALOCTIN A
c: RABBIT ANTI-$\alpha_2$-MACROGLOBULIN
1, 2, 3: HUMAN SERUM

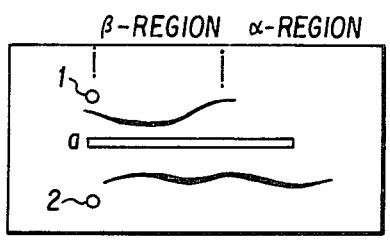

a: RABBIT ANTI-HUMAN C3 ($\beta_1C/\beta_1A$)
1: 5μl TEST MATERIAL WHICH CONSIST OF 0.9ml HUMAN SERUM AND 0.1ml OF PHYSIOLOGICAL SALINE SOLUTION
2: 5μl TEST MATERIAL WHICH CONSIST OF 0.9ml HUMAN SERUM AND 0.1ml OF 300μg/ml ALOCTIN A SOLUTION PREINCUBATED AT 37°C FOR 1 HOUR

FIG. 5c

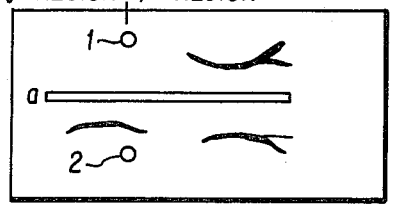

a: RABBIT ANTI-HUMAN C3 PROACTIVATOR
1: SAME AS WELL 1, FIG. 5c
2: SAME AS WELL 2, FIG. 5c

FIG. 5d

ALOCTIN A

BACKGROUND OF THE INVENTION

Field of the Invention

The present invention relates to a material known as Aloctin A which can be isolated from the plant Aloe, which is a plant belonging to Liliaceae. Aloctin A exhibits a variety of biological activities and therefore is expected to be medicinally useful.

SUMMARY OF THE INVENTION

An object of the present invention is to provide a material isolated from the plant, Aloe which exhibits a variety of useful medicinal properties.

Briefly, this object and other objects of the present invention as hereinafter will become more readily apparent can be attained by a material designated as Aloctin A which has the following characteristics:

(1) It possesses a molecular weight of approximately $1.8 \times 10^4$.

(2) Aloctin A is a glycoprotein having a protein to sugar ratio of 8 to 2 by weight.

(3) In SDS-polyacrylamide gel electrophoresis, Aloctin A gives a single band without 2-mercaptoethanol treatment and gives two discrete bands with 2-mercaptoethanol treatment, showing cleavage of the S-S bond in Aloctin A.

(4) Aloctin A has hemagglutinating and cytoagglutinating activity for transformed cells.

(5) Aloctin A has mitogenic acitivity and cap forming activity for lymphocytes and cultured transformed cells.

(6) Aloctin A reacts with some kind of serum proteins and forms precipitin lines in agarose gel plates.

(7) Aloctin A is capable of activating a complement third component (C3) via an alternative pathway.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3 shows the results of SDS-polyacrylamide gel electrophoresis of P-1 and Aloctin A fractions;

FIGS. 5a and 5b show the reactivity of Aloctin A with various serum proteins by immunoeletrophoresis;

FIGS. 5c and 5d show the activation of complement components in serum by Aloctin A through immunoelectrophoresis;

DESCRIPTION OF THE PREFERRED EMBODIMENTS

Aloctin A which is the material of the present invention, can be isolated from Aloe, a plant belonging to Liliaceae such as *Aloe arborescens* MILL, *Aloe perryi* BAKER, *Aloe barbadensis* MILLER and *Aloe forox* MILLER. The material is present in all parts of the plant, i.e., leaves, trunks, bark, seeds and the like, and can be isolated from these portions of the plant.

PURIFICATION

An example of a suitable method of isolation is as follows: The juice of 1,000 g crushed *Aloe arborescens* MILL leaves was filtered through gauze and then centrifuged at 10,000 rpm for 30 minutes to remove coarse material therefrom. The clear supernatant was subjected to ammonium sulfate fractionation. The fraction precipitated by 0–40% saturation with ammonium sulfate was dissolved in 0.05 M carbonate-bicarbonate buffer (pH 9.5) and dialyzed overnight against the same buffer to remove ammonium sulfate. The solution obtained was lyophilized, and the resulting dialized material, which is referred to as AS-40 hereinafter, demonstrated hemagglutinating activity. A small amount of 1 M acetic acid was added to the AS-40 solution in 0.05 M carbonate-bicarbonate buffer (pH 9.5) to give a pH of 4.4. Because of a change in pH, the previously clear AS-40 solution became cloudy. The cloudy solution was centrifuged at 10,000 rpm for 20 minutes. The supernatant, which is referred to as the Acidic sup hereinafter, was isolated from the precipitate, which is referred to as the Acidic ppt hereinafter. Greater agglutinating activity was detected in the Acidic sup than in Acidic ppt. Mitogenic activity for lymphocytes was detected only in the Acidic ppt.

Figure 1:
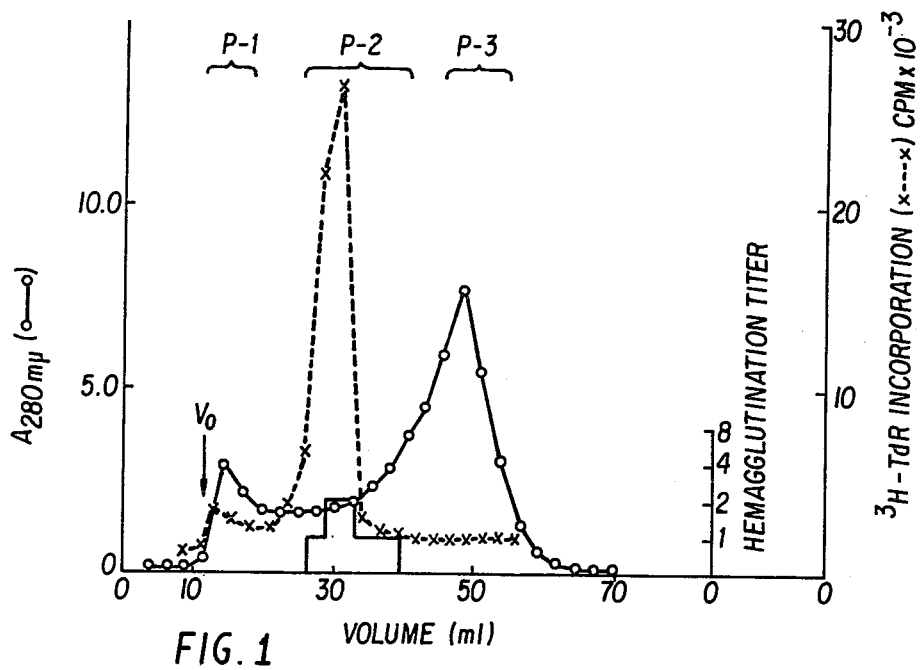
FIG. 1 shows the purification of Aloctin A by Sephadex G-200 gel filtration of Acidic precipitate.

The Acidic ppt was dissolved in a 0.05 M phosphate buffer (pH 8.0) after lyophylization, and filtered on a Sephadex G-200 (produced by Pharmacia Fine Chemical, Sweden) column (1.5×25 cm), previously equilibrated with the same buffer. The column was eluted at 4° C. with the same buffer at the flow rate of 2 ml per hour and 1.3 ml eluent fractions were collected. The elution curve of the protein obtained at A280 mμ is shown in FIG. 1. The elution volumes of Blue Dextran were determined and are indicated by the vertical arrow (Vo). Hemagglutinating activity is denoted by shaded portions and mitogenic activity is denoted by the dotted line. Hemagglutinating and mitogenic activities were detected in fractions obtained from 27.3 ml to 44.2 ml eluent (P-2), but were not detected in other fractions (P-1and P-3). The fractions from 27.3 ml to 44.2 ml eluent (P-2) contain the Aloctin A of the present invention.

Figure 2:
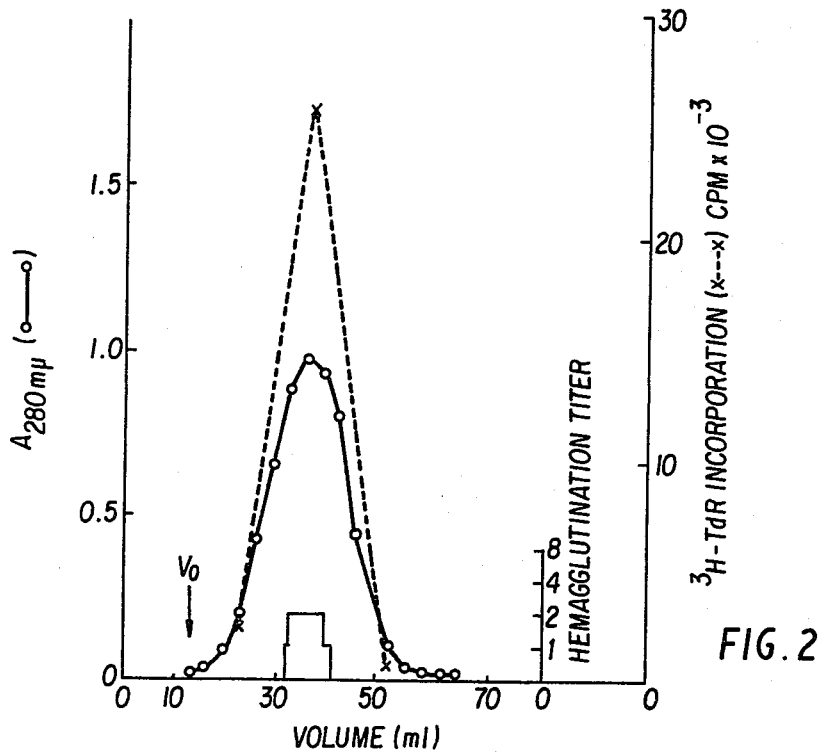
FIG. 2 shows the results of further purification of Aloctin A by Sephadex G-200 gel filtration.

The Aloctin A containing fractions were further purified by another chromatographic separation. The fractions from 27.3 to 44.2 ml eluent were in a sealed Spectrapor membrane tube (Spectrum Medical Industries, Inc. Calf., U.S.A.), and concentrated by covering the membrane tube with poly ethyleneglycol. The concentrated solution was re-filtered on Sephadex G-200 column (1.5×25 cm), previously equilibrated with 0.05 M phosphate buffer (pH 8.0). Elution was carried out at 4° C. with 0.05 M phosphate buffer (pH 8.0) at a flow rate of 2 ml/h, and fractions of 1.3 ml each were collected. The results are shown in FIG. 2 where hemagglutinating activity is indicated by the shaded portion (Vo:Void volume). The purified material is Aloctin A of the present invention.

The yield of protein, and the hemagglutinating and mitogenic activity of each fraction obtained from the purification process are summarized in Table I below.

TABLE I

Summary of Purification of Lectins From 1,000 g of Aloe leaves.

| Fraction | Total Protein | HA* activity[a] | HA* titer | HA* activity recovered | Mitogenic activity[b] |
|---|---|---|---|---|---|
| | mg | µg/ml | (per mg protein) | % | µg/ml |
| Juice | n.d.* | 500 | 2 | | n.d.** |
| AS-40 | 320.0 | 250 | 4 | 100 | n.d.** |
| Acidic ppt | 47.4 | 250 | 4 | 14.8 | 30.0 |
| P-1 | 1.05 | >1,000 | 0 | 0 | >100 |
| P-2 | 2.6 | 62.5 | 16 | 3.3 | 5.0 |
| Acidic sup | 18.4 | 125 | 8 | 11.5 | >100 |

[a]Minimum hemagglutinating dose against human erythrocytes
[b]Mitogenic dose to give 20,000 cpm of [methyl-$^3$H]thymidine incorporation against $1 \times 10^6$ lymphocytes
*Hemagglutination
**Not determined.

CHEMICAL AND PHYSICAL PROPERTIES

Chemical Analysis

Aloctin A gives positive results in the following qualitative protein and carbohydrate reactions, Nynhidrin reaction, Xanthprotein reaction, Molish-Udranszky reaction, Anthrone reaction, Fehlings reaction, Elson-Morgan reaction and the Periodic acid-Shiff reaction. Quantitative analysis shows that Aloctin A contains 18.3% neutral carbohydrate, suggesting that Aloctin A is a glycoprotein.

Elemental Analysis: C: 42.0–51.4 (%), H: 5.7–7.0 (%), N: 13.4–16.4 (%), O: 20.2–24.6 (%).

| IR-Sepctrum | |
|---|---|
| Wave Number | Strength of absorbance |
| 1,200–1,240 cm$^{-1}$ | medium |
| 1,500–1,520 | strong |
| 1,620–1,640 | strong |
| 3,200–3,260 | strong |

| $^{13}$C-NMR spectrum | |
|---|---|
| Chemical Shift | Spectral pattern |
| 15–27 ppm | broad, multiplet |
| 67–69 | sharp, singlet |
| 71–77 | sharp, multiplet |
| 99–100 | sharp, singlet |
| 169–180 | broad, multiplet |

Optical rotation

Optical rotation measurements were conducted at 470 nm in a cell 1 cm in length. A 7.7 mg/ml (calculated as bovine serum albumin) solution of Aloctin A in 0.05 M phosphate buffer (pH 8.0) exhibited a negative optical rotation at 25° C.

Disc Electrophoresis

Sodium dodecyl sulfate (SDS) polyacrylamide gel electrophoresis was conducted by the method of Weber and Osborn (Weber, K., and Osborn, M. (1969) J. Biol. Chem. 244, 4406–4412). Experiments were performed with samples some of which had been pre-treated with 2-mercaptoethanol. For estimation of molecular weight, the method of Segrest and Jackson (Segrest, J. P., Jackson, R. L. (1972) described in Methods in Enzymology, (Ginsburg, V. ed.) Vol, 28 (B), p. 54–63, Acad. Press, New York) was followed, using various concentrations of gel from 5% to 20.0%. For molecular weight standards, bovine serum albumin (BSA), ovalbumin, chymotrypsinogen A and cytochrome C were used. The gels were normally stained for protein with Coomassie brilliant blue and destained with a mixture of 10% acetic acid and 10% isopropanol.

SDS-polyacrylamide gel eletrophoresis of a 10% gel of the material isolated from P-1 fractions and Aloctin A without 2-mercaptoethanol treatment gave a single band as shown in FIGS. 3a and b. Electrophoresis was conducted with the gels in 0.1 M sodium phosphate buffer, pH 7.2, containing 0.1% SDS. The samples were heated at 100° C. for 5 minutes in 0.01 M sodium phosphate buffer, pH 7.2, containing 1% SDS, 25% glycerol and 0.001% bromphenol blue with and without 5% 2-mercaptoethanol. The material isolated from the P-1 fractions gave the same single band either with or without 2-mercaptoethanol treatment. Aloctin A, after 2-mercaptoethanol treatment, gave two discrete bands, a smaller peptide band ($\alpha$) and a larger peptide band ($\beta$) (FIG. 3c). From the above results it can be concluded that the $\alpha$ and $\beta$ peptides are subunits of Aloctin A.

Molecular Weight Estimation

Figure 4:
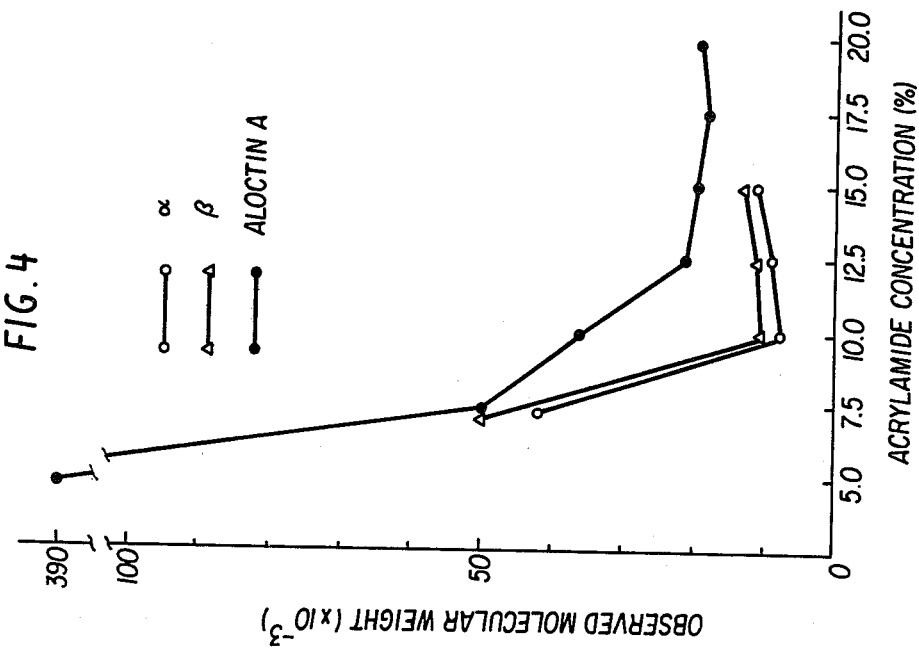
FIG. 4 is a graph of the molecular weight determination of Aloctin A using gel electrophoresis.

To obtain the molecular weight of Aloctin A, the method by Segret and Jackson was adopted using the following concentrations of gel: 5.0, 7.5, 10.0, 12.5, 15.0, 17.5 and 20.0%. SDS polyacrylamide eletrophoresis as described above was employed on gel samples. The mobility of the proteins was measured and the relationship between the logarithm of the molecular weights of several marker proteins and their mobilities were plotted. The molecular weight markers employed were: cytochrome C (MW 12,500), chymotrypsinogen (MW 25,000), ovalbumin (MW 45,000), bovine serum albumin (MW 67,000). The results are shown in FIG. 4. An asymptotic minimal molecular weight could be estimated from each curve in FIG. 4 and the following values were obtained: 18,000 for Aloctin A, 7,500 for $\alpha$ and 10,500 for $\beta$. However, these values are not complete because of the lack of correction of total carbohydrate amount in the glycoprotein molecule.

Amino Acid and Sugar Analysis

Samples of material were hydrolyzed in 6 N HCl in evacuated, sealed tubes at 110° C. for 20 hours. The amino acid content of the hydrolysates was determined in a Hitachi amino acid analyzer (KLA-3B) according to the method of Spackman et al. (Spackman, D. H., Stein, W. H., and Moore, S. (1958) Anal. Chem. 30, 1190–1206). Cysteine and cystine were identified as S-sulfocysteine by the method of Liu et al. (Liu, T. Y., and Inglis, A. S. (1972) in Methods in Enzymology (Hirs, C.H.W., and Timasheff, S. N., eds. Acad. Press, New York Vol. 25, p. 55–60). Tryptophan was not determined. The total amount of neutral sugars was determined by the orcinol-H$_2$SO$_4$ procedure (Winzler, R. J. (1956) in Method of Biochemical Analysis (Glick, D., ed. Vol. 2, p. 279–311 Interscience, New York).

The amino acid composition of Aloctin A is shown in Table II. In this experiment tryptophan was not determined. The most notable feature of the amino acid composition is a high proportion of acidic amino acids such as aspartic acid and glumatic acid and a low proportion of methionine and histidine.

Quantitative analysis shows that Aloctin A contains 18.3% of neutral carbohydrate, suggesting that Aloctin A is a glycoprotein.

BIOLOGICAL PROPERTIES

Hemagglutination Titration

Hemagglutination titrations were conducted with microtiter equipment (Cooke Lab. Prod., Virginia, U.S.A.). Human erythrocytes were treated with 0.1% trypsin for 1 hour, washed three times with phosphate buffered saline and a 2% suspension was used for assay. For the assay, 25 µl of a two-fold serial dilution of lectin solution were mixed with an equal volume of erythrocyte suspension and the mixture allowed to stand for 1 hour at room temperature with occasional shaking. The degree of agglutination was evaluated macroscopically and the titer value was defined as titer/mg protein.

TABLE II

Amino Acid Composition of Aloctin A and β-subunit

| Amino Acid | Aloctin A mole/mole of protein[a] | β-subunit |
|---|---|---|
| Aspartic acid | 27.50 (14)[b] | 7.93 (8)[b] |
| Threonine | 17.64 (9) | 3.63 (4) |
| Serine | 19.76 (10) | 4.57 (5) |
| Glutamic acid | 33.36 (17) | 7.51 (8) |
| Proline | 15.60 (8) | 4.47 (4) |
| Glycine | 30.68 (15) | 6.88 (7) |
| Alanine | 19.96 (10) | 6.72 (7) |
| Half-cystine | 7.94 (4) | 2.28 (2) |
| Valine | 18.16 (9) | 5.31 (5) |
| Methionine | 2.48 (1) | 1.18 (1) |
| Isoleucine | 14.64 (7) | 4.11 (4) |
| Leucine | 25.20 (13) | 6.61 (7) |
| Tyrosine | 9.80 (5) | 2.35 (2) |
| Phenylalanine | 6.12 (3) | 2.90 (3) |
| Lysine | 7.12 (4) | 3.79 (4) |
| Histidine | 5.68 (3) | 1.40 (1) |
| Arginine | 9.04 (5) | 2.64 (3) |

[a]Molecular weight of Aloctin A was taken as 18,000.
[b]Number of residues to the nearest integer.

Hemagglutinating Activity

Aloctin A agglutinates erythrocytes of various species such as human, sheep and rabbit, and does not show A-B-O blood group specificity in hemagglutination tests in the human system. Treatment of human erythrocytes with 0.1% trypsin increases the agglutination approximately five-fold compared with non-treated erythrocytes. The minimum hemagglutination doses of the purified fractions on trypsin-treated human erythrocytes are shown in Table I.

Cytoagglutinating Activity

A cytoagglutination titration was conducted in the same manner as the hemagglutination titration in comparison with concanavalin A (Con A). The results are shown in Table III. As shown, Aloctin A exhibits a cytoagglutination titer analogous to that of Con A against various cell lines. However, a very high titer was recorded for Aloctin A in X-ray induced thymoma. Generally, highly malignant transformed cell lines such as P3-J, Molt-4B, X-ray induced thymoma, KB, HeLa S-3 and CHO-K1 possessed higher cytoagglutination titers than cells of lower malignancy or normal cells (not malignant) such as NC-37, DON-6, NR-K and NS-2.

TABLE III

Cytoagglutination Titer

| Cells | Con A | | Aloctin A | |
|---|---|---|---|---|
| NC-37 | 4 | | 4 | |
| P3-J | 32 | | 32 | |
| P3HR-1 | 32 | | 32 | |
| Molt-4B | 32 | | 32 | |
| M.Spleen Cell | 32 | | 32 | |
| Xray-thymoma | 64 | | 256 | |
| | T-E* | E** | T-E* | E** |
| KB | 32 | 16 | 32 | 16 |
| HeLa-S3 | 32 | 16 | 32 | 16 |
| Don-6 | 4 | 2 | 1 | 1 |
| CHO-K1 | 16 | 16 | 64 | 32 |
| HNG-100 | 32 | 32 | 64 | 32 |
| NR-K | 16 | 4 | 8 | 4 |
| NS-2 | 4 | 2 | 8 | 4 |
| REWKA2 | 16 | 16 | 16 | 16 |

*Treatment with a mixture of 0.05% trypsin and 0.02% EDTA.
**Treatment with 0.02% EDTA.

Mitogenic Activity

Preparation of Human Lymphocytes

Normal human venous blood was withdrawn into syringes previously loaded with heparin. Purified lymphocytes were obtained by the method of Kawaguchi et al (Kawaguchi, T., Matsumoto, I., and Osawa, T. (1973) J. Biol., Chem. 249, 2786–2792). The cells were then washed with 0.25% bovine serum albumin in 0.15 M NaCl-0.01 M phosphate buffer (pH-7) and used for examination of mitogenic activity.

Assay of Mitogenic Activity

A morphological examination of lymphocyte transformation was conducted by determining the percentage of transformed cells in a Giemsa-stained preparation, counting approximately 1,000 cells per mitogen sample.

An assay of [$^3$H]thymidine incorporation was performed by adding [methyl-$^3$H]thymidine (2.0µCi, The Radiochemical Center, England) to each tube containing lymphocytes ($1 \times 10^6$ lymphocytes/ml, 2 ml) after incubation with a mitogen sample for six hours. Sixty hours after the addition of [methyl-$^3$H]thymidine, the cells were collected and washed three times with cold phosphate buffered saline (pH 7.2). After adding 1.5 ml of cold 5% TCA and 2 ml cold methanol to the cell pellet, one drop of 3% bovine serum albumin (BSA) as carrier protein was added. The precipitate was washed on a membrane (GF/C 2.5 cm, Whatman) in a "Manifold" multiple sample collector (Millipore). To the dried membranes, 0.3 ml solubilizer (Soluene TM 100, Packard) was added and the membranes were incubated at 37° C. for two hours, and 5 ml of scintillation fluid (5 g PPO and 0.1 g POPOP in 1,000 ml toluene) was added to each membrane. The radioactivity was counted in a Beckman LS-200B liquid scintillation counter.

Seventy two hours after the culture of human lymphocytes with Aloctin A or Acidic ppt, large lymphocytes with morphologically transformed shapes were abundant compared to culture systems of purified β-subunits and those without mitogen. When approximately 1,000 cells were counted, about 70% of the lymphocytes were found to be transformed after 72 hours culture. This degree of transformation is almost the same as that by phytohemagglutinin-W (PHA-W, Wellcome Co., U.S.A.) which was tested as a positive control.

In order to demonstrate [methyl-$^3$H]thymidine incorporation as a function of the mitogen, lymphocytes were treated with various quantities of Aloe fractions such as Acidic ppt, $\beta$-subunit and Aloctin A.

As shown in Table I, mitogenic activity was detected in both Acidic ppt and Aloctin A. Among the purified fractions Aloctin A along displayed mitogenic activity.

Cap forming Activity in Various Cell Membranes

Corelated to mitogenic activity, the cap forming activity of Aloctin A on membranes of lymphocytes and other various cell lines were examined in comparison to Con A.

Fluorescence-labeled Aloctin A (FITC-Aloctin A) was prepared by the method of Cebra and Goldstein (Cebra, J. J. & Goldstein, G. (1965) J. Immunol., 95, 230-245). Cells were stained with FITC-Aloctin A at 37° C. for 40 minutes, after washing the cells with phosphate buffered saline, and were observed by fluorescence microscopy. The results are shown in Table IV.

TABLE IV

| Cells | Ratio of cells with caps (%) | |
|---|---|---|
| | FITC-Con A | FITC-Aloctin A |
| N.H.P.L.* | | 35 |
| P3HR-1 | 14 | 25 |
| Molt-4B | 20 | 49 |
| KB | 12 | 60 |
| HeLa-S3 | 30 | 45 |
| Don-6 | 0 | 0 |
| CHO-K$_1$ | 0 | 30 |
| HNG-100 | 0 | 37 |
| NR-K | 0 | 6 |
| NS-2 | 12 | 31 |
| REWKA$_2$ | 13 | 48 |
| M.**spleen cell | 48 | 42 |
| X-ray-thymoma | 20 | 31 |

*Normal human peripheral lymphocytes.
**Mouse

As shown, it is evident that Aloctin A possesses cap forming activity on not only lymphocytes but also various cultured cells. Among all tested cells, only Don-6 cells which are not malignant showed no cap formation. From these results it is believed that an Aloctin A receptor is present in lymphocytes and malignant cells, and by the formation of a receptor-Aloctin A complex, redistribution of the complex is stimulated.

Reactivity with Serum Proteins

Immunodiffusion was performed by the Ouchterlony method (Ouchterlony, O. (1953) Acta Path. Microbiol Scand. 32, 231-240), using 1.0% Agarose II (Dojin-do Laboratories, Japan) in 0.05 M phosphate buffer, pH 6.5. Immunoelectrophoresis was performed by the Hirschfeld technique (Hirschfeld, J. (1960) Sci. Tools 7, 18-25), using 1.4% Agarose II in 0.025 M veronal buffer, pH 8.6.

The reactivity of the crude extract of Aloe against various sera by the gel diffusion test (Ouchterlony test) was previously reported (Fujita, K., Suzuki, I., Ochiai, J., Shinpo, K., Inoue, S., and Saito, H. (1978) Experientia 34, 523-524). Sixteen sera of specimens such as human, rabbit, goat, dog, cat, horse, pig, rat, fetal rat, bovine, fetal calf, snake and snapping turtle were tested, and all of them showed positive reactivity. The extract of Aloe reacted not only with mammalian sera but also with fish, amphibia, as well as reptilia. Moreover, more than two precipitin lines wee detected in almost all sera tested.

Among purified fractions of P-1 ($\beta$-subunit) and Aloctin A, only Aloctin A reacted with human serum proteins, and two precipitin lines were detected (FIG. 5a). The two precipitin lines are indicative of two serum proteins reacting with Aloctin A. The center well is normal rabbit serum, well 1 is $\beta$ (1 mg/ml), well 2 is Aloctin A (1 mg/ml), well 3 is S-1 (1 mg/ml), well 4 is S-2 (1 mg/ml). Through immunoelectrophoresis using human serum, $\alpha_2$-macroglobulin was found to be one of the serum proteins that reacted with Aloctin A (FIG. 5b). In the immunoelectrophoresis experiment the anode was positioned to the right while the cathode was on the left. Precipitin reactions developed against rabbit anti-human serum (upper portion), rabbit anti-human $\alpha_2$-macroglobulin (lower portion), and Aloctin A (middle portion, arrow). The immunoelectrophoresis indicates that the electric mobility of the precipitin lines of human serum protein against Aloctin A (arrow) completely coincides with that of $\alpha_2$-macroglobulin. Wells 1 and 2 are human serum, trough a is rabbit anti-human serum, trough b is Aloctin A solution in 0.05 M phosphate buffer (300µg/ml), trough c is rabbit anti-$\alpha_2$-macroglobulin.

Activation of Serum Complement Components by Aloctin A

When the C3 component or the C3 proactivator is activated, there is a change in electrophoretic mobility; the C3 component ($\beta$1C) moves to the $\beta$ regin, while the activated C3 component $\beta$1A) shifts to the $\alpha$ region. C3 proactivator is seen in the $\beta$ region in agarose electrophoresis but it moves to the $\gamma$ region when the C3 proactivator is activated. FIGS. 5c and 5d show the immunoelectrophoretic mobility of the C3 component and the C3 proactivator of human serum incubated with Aloctin respectively at 37° C. for one hour. Well 1 is 5 µl of test material which consists of 0.9 ml of human serum and 0.1 ml of physiological saline solution. Well 2 is 5 µl of a test material which consists of 0.9 ml of human serum reacted with 0.1 ml of 300 µg/ml P-2 solution at 37° C. for one hour. The trough is rabbit anti-human C3 ($\beta_1$C/$\beta_1$A). In the case of human serum treated with Aloctin A, an immunoprecipitin line against rabbit anti-human C3 ($\beta_1$C/$\beta_1$A) serum was observed in the $\beta$ and $\alpha$ regions, whereas, in the non-treated human serum, the immunoprecipitin line was found only in the $\beta$ region. The immunoelectrophoretic pattern of C3 proactivator in human serum reacted with Aloctin A is shown in FIG. 5d. Immunoelectrophoresis was conducted as described for FIG. 5c. Precipitin reactions developed against rabbit anti-human C3 proactivator. Well 1 contains the same test material as in well 1 of FIG. 5c, and well 2 contains the same test material as in well 2 of FIG. 5c. The trough contains rabbit anti-human C3 proactivator. A precipitin line of human serum treated with Aloctin A against rabbit anti-human C3 proactivator was observed in the $\beta$ and $\gamma$ regions, whereas, the precipitin line of non-treated human serum was found only in the $\beta$ region.

It is well known that a complement system is activated via either the classical or alternate pathway (Sandberg, A. L., Osler, A. G., Shin, H. S., and Oliverira, B. (1970) J. Immunol. 104, 329-334; Gewurz, H., Shin, H. S., and Mergenhagen, S. E. (1968) J. Exp. Med. 128, 1049-1057; Marcus, R. L., Shin, H. S., and Mayer, M. M. (1971) Proc. Natl. Acad. Sci. 68, 1351-1354; and Frank, M. M., May, J., Gaither, T., And Ellman, L. (1971) J. Exp. Med. 134, 176–187) and that only $Mg^{++}$ is necessary for the alternate pathway, while both $Mg^{++}$ and $Ca^{++}$ are essential for the classical pathway. It was attempted to determine whether Aloctin A acts through the classical or the alternate pathway. To 1 ml of fresh human serum was added 0.1 ml of Aloctin A suspension (1 mg/ml). The mixture was incubated at 37° C. for one hour and then centrifuged at 5,000 rpm for 30 minutes in the cold. The supernatant was used for immunoelectrophoresis to test the complement activation. The precipitin line of C3 proactivator converted in the presence of EGTA (ethyleneglycol-bis-N,N'-tetraacetic acid) was observed in the $\gamma$ region, but it was not observed in the presence of EDTA. Moreover, activation of the complement components depended upon the temperature. An examination was conducted to determine whether Aloctin A activates C1, C2 and C4 by the method of Takada et al, (Takada, Y., Arimoto, Y., Mineta, H., and Takada, A., (1968) Immunology 34, 509–515). The results showed no activation of C1, C2 and C4. These results suggest that the activation of complement components by Aloctin A occurs via the alternate pathway.

USE AS AN ANTI-TUMOR AGENT

It is clear that Aloctin A possesses strong anti-tumor activity from the following experiments.

Figure 6:
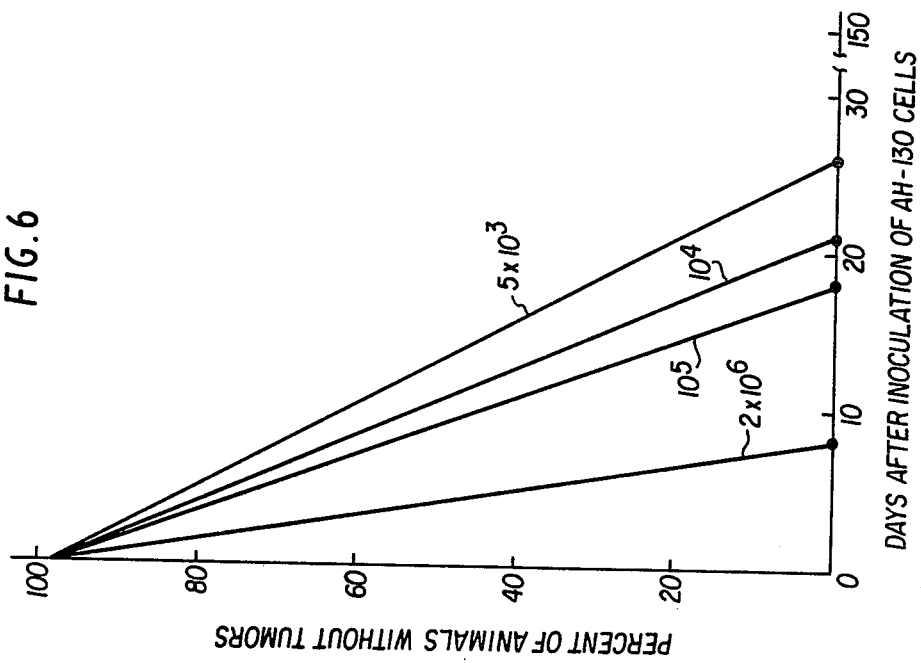
FIG. 6 is a graph showing the effect of tumor development in rats injected with AH-130 cells.
Figure 7:
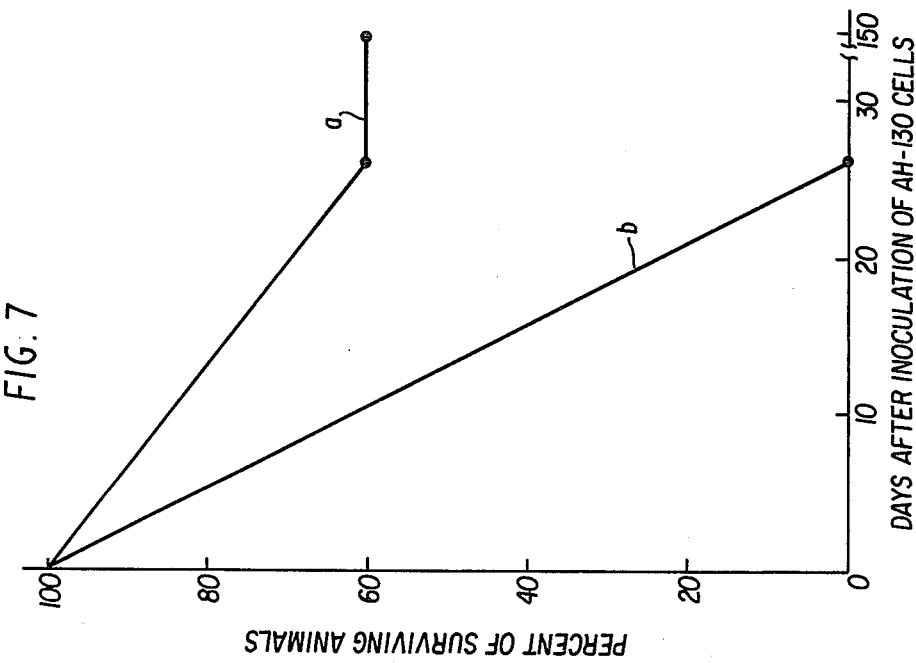
FIG. 7 is a graph showing the survival rate of rats injected with an Aloe preparation versus a control.

Donryu inbred rats weighing about 100 g were used for the anti-tumor assay. The tumorigenicity of AH-130 cells after intra-peritoneal implantation of $5 \times 10^3$ to $2 \times 10^6$ cells into 30 to 40 day old rats had been initially examined. All animals were dead with transplants tumor after 8 to 27 days (FIG. 6). Seven day old AH-130 ascites cells, $5 \times 10^3$ cells in 0.5 ml doses, were injected intraperitoneally into rats. The effect on transplanted tumor development of Acidic ppt injected prior to transplanted tumor cell implantation was examined. The results obtained are shown in FIGS. 7a and 7b.

a: Rats were intraperitoneally injected with 2 mg of Acidic ppt (2 mg protein) every day for 7 days, and then $5 \times 10^3$ AH-130 cells were injected 7 days after the last injection of Acidic ppt.

b: Control; Rats were not injected with an Aloe preparation and were implanted with $5 \times 10^3$ AH-130 cells.

Figure 8:
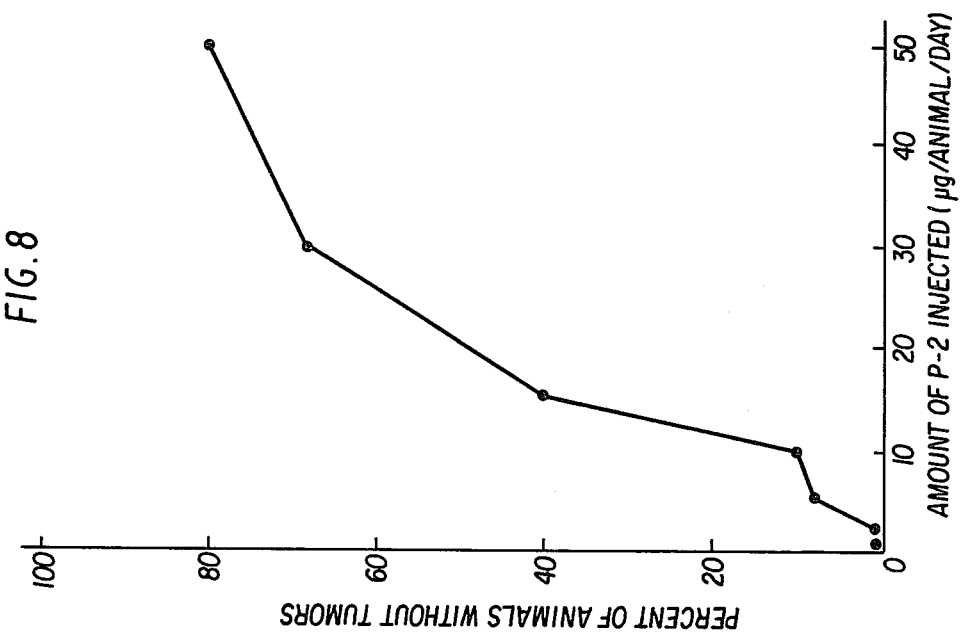
FIG. 8 is a graph showing the dose response of rats treated with Aloctin A versus survival rate.

The next experiment was performed to determine the dose response of Aloctin A relative to the survival time of transplanted tumor cell implanted animals. Various amounts of Aloctin A were injected every day for 7 days from 14 days to 7 days prior to transplanted tumor cell implantation, and the results obtained from the animals were scored after 80 days, that is, 54 days after the last control animal with transplanted tumor had died. The results are shown in FIG. 8. FIG. 8 shows the number of surviving animals without transplanted tumors. The anti-tumor activity of Aloctin A varies according to dose. Each percentage point in the results is the average of 25–30 animals from three experiments. Furthermore, ten rats, which were injected with 50 μg of Aloctin A every day for 7 days and which survived for 120 days after transplanted tumor cell implantation, were re-implanted with $1 \times 10^5$ AH-130 cells. The transplanted tumors regressed completely in all tested rats.

In another test, JCL-ICR mice weighting about 30 g were used. The mice were injected with $2 \times 10^5$ sarcoma 180 cells maintained as ascites form into the right shoulder subcutane. After the transplanted tumor cell implantation, the mice were injected daily with 30 μg of an isotonic solution of Aloctin A for two weeks. After 60 days, the inhibition ratio was calculated as 80% and complete regression of the transplanted tumor was 2/10.

The glycoprotein, Aloctin A is non-toxic, and nothing remains after the complete regression of the transplanted tumors in the tested animals within the dosage ranges in the present experiments.

Having now fully described this invention, it will be apparent to one of ordinary skill in the art that many changes and modifications can be made thereto without departing from the spirit or scope of the invention as set forth herein. ACCORDINGLY,

What is claimed as new and intended to be secured by Letters Patent is:

1. A glycoprotein isolated from Aloe, a plant belonging to Liliaceae,
    (1) having a molecular weight of $1.8 \times 10^4$ and a ratio of protein to sugar of 8 to 2 by weight;
    (2) yielding only a single band upon SDS-polyacrylamide gel electrophoresis without 2-mercaptoethanol treatment and yielding two discrete bands upon SDS-polyacrylamide gel electrophoresis with 2-mercaptoethanol treatment;
    (3) having hemagglutinating and cytoagglutinating activity for transformed cells;
    (4) having mitogenic activity for lymphocytes, cap forming activity for lymphocytes and cultured transformed cells using fluorescence labeled glycoprotein;
    (5) having binding reactivity with some types of serum proteins;
    (6) having the capability of activating serum complement components;
    (7) having an infrared spectrum whose absorption peaks appear at 1200–1240 $cm^{-1}$, 1500–1520 $cm^{-1}$, 1620–1640 $cm^{-1}$ and 3200–3260 $cm^{-1}$; and
    (8) having a nuclear magnetic resonance spectrum whose absorption peaks appear at 15–27 ppm (multiplet), 67–69 ppm (singlet), 71–77 ppm (multiplet), 99–100 ppm (singlet) and 169–180 ppm (multiplet).

* * * * *